(12) United States Patent
Sjöblom

(10) Patent No.: US 6,753,014 B1
(45) Date of Patent: Jun. 22, 2004

(54) METHOD TO OBTAIN MICROPARTICLES

(75) Inventor: Brita Sjöblom, Hovås (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/674,043

(22) PCT Filed: Sep. 1, 2000

(86) PCT No.: PCT/SE00/01682

§ 371 (c)(1),
(2), (4) Date: Oct. 23, 2000

(87) PCT Pub. No.: WO01/19345

PCT Pub. Date: Mar. 22, 2001

(30) Foreign Application Priority Data

Sep. 10, 1999 (SE) .............................................. 9903236

(51) Int. Cl.[7] .................................................. A61K 9/16
(52) U.S. Cl. ...................................... 424/489; 424/486
(58) Field of Search ................................ 424/489, 490, 424/486

(56) References Cited

U.S. PATENT DOCUMENTS 5,017,383 A * 5/1991 Ozawa et al. ................ 424/490
5,102,983 A * 4/1992 Kennedy ..................... 424/486

FOREIGN PATENT DOCUMENTS

| | | | |
|---|---|---|---|
| GB | 2329124 | | 3/1999 |
| GB | 2329124 A | * | 3/1999 |
| WO | 9013285 | | 11/1990 |

* cited by examiner

Primary Examiner—James M. Spear
Assistant Examiner—MP Young
(74) Attorney, Agent, or Firm—White & Case LLP

(57) ABSTRACT

Method of obtaining microparticles.

A method for the preparation of homogeneous microparticles containing a pharmaceutically active substance by a spray freezing technique wherein the medium to be atomized into droplets has a high dry content and comprises besides the active substance a polymer and a liquid (in which the polymer may be soluble) in which the active substance and polymer are suspended, dissolved or emulsified.

23 Claims, No Drawings

METHOD TO OBTAIN MICROPARTICLES

FIELD OF INVENTION

The present invention provides a method of obtaining microparticles by a spray freezing technique. More specifically the present invention relates to a method by which spherical microparticles containing one or more pharmaceutically active substances can be prepared.

BACKGROUND OF THE INVENTION

The strategy for pharmaceutical formulation of a given drug depends on different factors. Ultimately, these factors emanate from 1) the therapeutic needs, 2) the physical chemical properties of the drug, and 3) the influence of the biological environment where the formulation will release its contents. Thus, both technical and biopharmaceutical considerations will contribute to a successful therapy.

However, improved drug administration may also be achieved by so called modified release of the drug, which has been discussed extensively in the literature, e g R L Langer and D L Wise (Eds) *"Medical Applications of Controlled Release"*, vols I, II (1984), CRC Press Inc, Boca Raton.

Several approaches to achieve different types of modified release are described in the references above. Of special importance to the present invention is modified release achieved by formulating the active substance with a suitable carrier material in the form of microparticles. Such a formulation then contains multiparticulate discrete delivery units, each of which can be coated if necessary with, e g a suitable pH sensitive, semipermeable or other polymeric film. Several advantages can be obtained with this type of formulation compared with more conventional delivery means. Thus, the small size of the

FIELD OF INVENTION

The present invention provides a method of obtaining microparticles by a spray freezing technique. More specifically the present invention relates to a method by which spherical microparticles containing one or more pharmaceutically active substances can be prepared.

BACKGROUND OF THE INVENTION

The strategy for pharmaceutical formulation of a given drug depends on different factors. Ultimately, these factors emanate from 1) the therapeutic needs, 2) the physical chemical properties of the drug, and 3) the influence of the biological environment where the formulation will release its contents. Thus, both technical and biopharmaceutical considerations will contribute to a successful therapy.

However, improved drug administration may also be achieved by so called modified release of the drug, which has been discussed extensively in the literature, e g R L Langer and D L Wise (Eds) *"Medical Applications of Controlled Release"*, vols I, II (1984), CRC Press Inc, Boca Raton.

Several approaches to achieve different types of modified release are described in the references above. Of special importance to the present invention is modified release achieved by formulating the active substance with a suitable carrier material in the form of microparticles. Such a formulation then contains multiparticulate discrete delivery units, each of which can be coated if necessary with, e g a suitable pH sensitive, semipermeable or other polymeric film. Several advantages can be obtained with this type of formulation compared with more conventional delivery means. Thus, the small size of the microparticles assures a fast and predictable emptying from the stomach, which is of special importance in the presence of food. Further, the particles will spread over a larger area in the whole GI-tract compared with a conventional monolithic (single-unit) formulation. This will result in a safer therapy when the active substance has local irritating side effects. Controllable plasma levels of absorbed drug can also be obtained. The microparticle formulation will also have a longer residence time in the colon which makes 24 hrs extended release formulations possible. From a technological point of view, microparticles are more suitable for coating and handling since a technical fault during the process may be serious for single unit formulations but less so for micropellets. Also, microparticle formulations are more easily manufactured and prepared in different doses than standard tablet systems.

PRIOR ART

An ideal method for the preparation of microparticles where the drug is homogeneously distributed within a polymeric matrix, should be simple, reproducible, rapid and minimally dependent on the solubility characteristics of the drug. A high product yield and a high degree of retention of the active substance in the final microparticles should also be obtained.

Several different techniques are available for making microparticles (<1 mm), e g spray-drying, extrusion-spheronization, spray-chilling, emulsion solvent evaporation/extraction and coating of nonpareil spheres, among others. A recent review was presented by Conti et al in STP Pharma Sci 7, 331 (1997) where the technical aspects of coacervation, spray-drying, emulsion solvent extraction, and emulsion solvent evaporation were discussed.

However, all existing techniques suffer from one or more drawbacks. Thus, many drugs are sensitive to heat and therefore will deteroriate which restricts the use of spray-drying or spray-chilling.

In extrusion spheronization and in coating of non-pareils particles it has been difficult to achieve acceptable microparticles in the size range of 50–400 $\mu$m. Pellets made by these methods contain significant amounts of inert excipients. This may make the pelletization of high-dose drugs by these methods a difficult task.

Finally, in emulsification solvent evaporation, an emulsion has to be made and the drug to be incorporated is preferably lipophilic, which restricts the drugs which can be used. Another drawback is the toxicity of the solvent used, usually methylene chloride, which can remain in the microparticles after drying.

However, despite the many different approaches there has not been disclosed a technique that can produce both smaller microparticles but also particles of more uniform size. It is important to avoid, e g segregation and dose variation during further processing into capsules or tablets. Further, the existing techniques do not incorporate several desirable aspects such as the possibility to produce spherical microparticles of different size ranges that are homogeneous, have a high drug content and sufficient mechanical strength (to e g withstand coating processes) into one single technique.

A spray-freezing technique has been used for the processing and granulation of ceramic materials to achieve homogeneous distribution of additives within granules to be compacted. For the processing of slurries containing silicon-nitride, sintering additives and a binder, spherical free-flowing granules have been prepared by spray-freezing and subsequent freeze-drying. The homogenity of the slurry was retained in the granules and thus in the final sintered product (Nyberg et al, Euro-Ceramics II 1, 447 (1993)). Suspensions of silicon carbide and additives were processed in this way to give granules for compaction (U.S. Pat. No. 4,526,734). The increased homogenity compared with traditional granulation techniques resulted in better mechanical properties of a whisker reinforced ceramic (EP 0 584 051). The process is also feasible for making homogeneous powder blends for ceramic superconductors (Japanese unexamined patent application no. 59-102433).

Normally pharmaceutical materials are lyophilized by freeze-drying in a bulk process in which the solution/suspension to be freezed is placed in vials or on trays in a freeze-drier, where freezing and subsequent sublimation of the dry solvent take place. The dried product is a powder cake.

The rapid freezing provided by spray-freezing ensures that no concentration gradients exist in the resulting frozen particles and degradation of biological material is prevented. This approach has been used to achieve precise metering and dispensing (M J Akers and D J Schmidt, BioPharm 28, (April 1997)); where the frozen particles were in the form of large lumps of size 1–9 mm. Freezing of droplets in a moving bath of Freon 12 (−20° C.), which medium conflicts with environmental demands, has been used to obtain porous, free-flowing, spherical granules with rapid dissolution (U.S. Pat. No. 3,932,943); as well as making homogenous granules for tableting with precise dosing (U.S. Pat. No. 3,721,725).

A process for preparing foamed bioabsorbable polymer particles for surgical use was presented in U.S. Pat. No. 5,102,983. Here, however, the porosity was very large, and the pore sizes in the range of 4–10 $\mu$m, the dry content of the solution being sprayed being 1–20 wt %.

U.S. Pat. No. 5,019,400, disclosed the use of a mixture of a biologically active material, a polymer, and a solvent which was sprayed into a non-solvent cooling medium that freezed the droplets with subsequent extraction of the solvent in the droplets during heating. The particles were finally dried in a vacuum-drier. The microparticles formed were porous, and contained 0.01–50% of the active substance. The dry content of the solution sprayed was 6 wt %. This process is not entirely satisfactory since it is an advantage to have one single drying step after freezing and also a higher active substance content than 50 wt % in order to make high dose materials.

U.S. Pat. No. 5,405,616 discloses a method of forming droplets by forcing a suspension/solution/emulsion through calibrated jets. The droplets then fall into liquid nitrogen. Due to low shear forces the size of the pellets formed is large; 0.2–12 mm, which would then give a less safe dosability than if smaller particles could have been achieved. The smallest particles achieved were 0.8–1 mm. Further, to achieve low friability pellets, the drying step after freeze-drying was performed by thawing the pellets before conventional vacuum drying. To achieve these low friability pellets the matrix former is restricted to materials that during thawing will form a gel. The particles obtained contain no more than 33 wt % of the active substance.

To the skilled person particle production utilizing the technique described in U.S. Pat. No. 5,405,616 appears to be quite a slow process and not suitable for large scale industrial pharmaceutical production.

OBJECT OF THE INVENTION

An object of the present invention is to provide a method for the production of microparticles. More specifically, the method is for the production of homogeneous microparticles which does not have the drawbacks of the methods discussed above, e.g. methods that rely on heat or multiple solvents for drug dissolution, but instead puts no restrictions on the drug to be incorporated. A further object is to provide a method for the production of microparticles with controllable amounts of incorporated drug in a high-yield process. Also, the invention provides a method to produce homogeneous microparticles with an incorporated drug that have low friability so that they for instance can withstand coating processes. A further object of the invention is to provide a method to produce microparticles that have easily controllable density and strength. A further object is to obtain microparticles with a high content of active substance.

DISCLOSURE OF THE INVENTION

It has now been found that free-flowing, homogeneous microparticles having low friability can be obtained by spray-freezing a suspension, solution or emulsion of a pharmaceutically active substance with subsequent freeze-drying of the frozen microparticles. The microparticles are preferably spherical in shape. The porosity of the microparticles obtained is controlled in the process by the dry content of the suspension, solution or emulsion. Apart from the porosity, the brittleness of the microparticles is controlled by the amount of polymer binder included in the suspension, solution or emulsion. In order to obtain low friability particles the dry content of the suspension or solution or emulsion should be high.

Generally the following conditions are applicable to obtain low friability microparticles according to the method of the invention;

Low friability microparticles, that can for instance withstand coating with a polymeric film, are achieved when the suspension, solution or emulsion has a dry volume content of at least 15 vol %, preferably up to 60 vol %, and a polymer binder content of at least 5 weight %, preferably 10 weight % or more, and more preferably 15 weight % or more (based upon dry content). A high total pharmaceutically active substance content can be obtained by using the present invention, such as up to 95 weight % or preferably 90 weight % (based upon dry content). The median pore size of the microparticles obtained being preferably a maximum of 1.0 $\mu$m. Dry content and dry volume content are weight % and volume %, respectively, of dry material in the suspension/solution/emulsion (dry/(dry+liquid)), wherein the dry material is pharmaceutically active substance+polymer.

According to the present invention homogenous low friability microparticles can be obtained when the dry content is from 15 to 60 vol % and the polymer binder content is 5 weight % or more giving dry microparticles with a relative density of 15 to 60% (a porosity of 85 down to 40 vol %). [Relative density: weight of freeze-dried material/volume of freeze-dried material/theoretical density of dry material].

The content of the pharmaceutically active substance calculated on the weight of the dried microparticles may be from 60 to 95 weight %, preferably from 75 to 90 weight %.

The dry content of the liquid medium is defined as the residue after drying at 110° C. for 2 hours, divided by the total amount before drying. The dry content can be expressed either as weight percent or, preferably, as volume percent.

The success in obtaining low porous microparticles and thus low friable microparticles depends on the volume fraction of dry material and the amount of polymer binder. The dry content of a suspension/solution/emulsion should thus preferably be expressed as a volume fraction although this cannot always be calculated.

The microparticles may be obtained by spraying a homogeneous suspension, solution or emulsion of the active subtance(s) through an atomizer into a vessel with a cold medium with a temperature well below that of the freezing point of the liquid in the droplets. Frozen droplets will then form instantaneously. The structure of the suspension, solution or emulsion is retained in the droplets providing a homogeneous distribution of the substances within the droplets. The frozen liquid is then sublimated by freeze-drying of the frozen droplets where the structure of the droplets is retained due to lack of migration of substances during drying.

The following general steps of the procedure are further exemplified in the Experimental Section below:

a) Preparation of a medium for atomizing. The medium is a suspension, a solution or an emulsion of the active substance. A suspension may be prepared by dissolving or dispersing a polymer in a liquid (as defined below), and then adding fine particles of the active substance. A farther dispersing agent (typically in an amount of less than 20% (w/w) of the polymer amount) might also be included to facilitate the dispersion of the active substance. The polymer might then act as a binder between the fine active substance particles in the microparticles and can be either a water soluble or a non-water soluble polymer, according to definitions below.

b) Atomizing of the suspension/solution/emulsion into droplets. The suspension, solution or emulsion is fed by e.g. a peristaltic pump through a nozzle that could be a pneumatic nozzle, an ultrasonic nozzle, a rotary atomizer or a pressurized nozzle. A typical size distribution of spheres produced by this process can range from 1000 μm down to 10 μm.

c) Freezing of the formed droplets: The atomizer is situated above the cold medium in a cylindrical vessel. If the cold medium is a liquified gas the droplets in the spray formed by the nozzle hit the cold boiling gas before hitting the cold medium that is stirred to get a better wetting of the droplets. Instant freezing takes place and the structure of the homogeneous suspension is retained within the frozen microparticles.

d) Sublimation of the frozen liquid within the droplets: The frozen droplets are transferred from the cold medium to a freeze-drier to sublimate the frozen liquid. This step takes place without any shrinkage of the droplets or migration of excipients (e g polymers) and thus the structure of the suspension/solution/emulsion is retained within the dry microparticles.

The polymer or dispersing agent used for the formulation may be a dry polymer that is partly or fully soluble in the liquid. The polymer or dispersing agent used might also be a dispersion of polymer particles (e g a latex).

The polymer or dispersing agent could be but are not limited to the excipients listed below.

cellulose derivatives, like ethylcellulose, hydroxypropyl methyl cellulose, hydroxyethyl cellulose, hydroxypropyl cellulose, ethyl hydroxyethyl cellulose, carboxymethyl cellulose, cellulose acetate butyrate, cellulose acetate phtalate, methylcellulose, etc other polysaccharides, like alginate; xanthan; carrageenan; scleroglucan; pullulan; dextran; hyaluronic acid; chitin; chitosan; starch; etc other natural polymers, like proteins (e g albumin, gelatin, etc); natural rubber; gum arabic; etc synthetic polymers, like acrylates (e g polymethacrylate, poly(hydroxy ethyl methacrylate), poly(methyl methacrylate), poly(hydroxy ethyl methacrylate—co methyl methacrylate), Carbopol® 934, etc); polyamides (e g polyacrylamide, poly(methylene bisacrylamide), etc); polyanhydrides (e g poly(bis carboxyphenoxy)methane, etc); PEO-PPO block-co-polymers (e g poloxamers, etc); polyvinyl chloride; polyvinyl pyrrolidone; polyvinyl acetate; polyvinyl alcohol; polyethylene, polyethylene glycols and co-polymers thereof; polyethylene oxides and co-polymers thereof; polypropylene and co-polymers thereof; polystyrene; polyesters (e.g. poly(lactic acid), poly(glycolic acid), poly(caprolactone), etc, and co-polymers therof, and poly(ortho esters), and co-polymers thereof); polycarbonate; cellophane; silicones (e.g. poly (dimethylsiloxane), etc); polyurethanes; synthetic rubbers (e.g. styrene butadiene rubber, isoprotene rubber, etc); etc surfactants, e.g. anionic, like sulphated fatty alcohols (e g sodium dodecyl sulphate), sulphated polyoxyethylated alcohols or sulphated oils, etc; cationic, like quaternary ammonium and pyridinium cationic surfactants, etc; non-ionic, like polysorbates (e.g. Tween), sorbitan esters (e.g. Span), polyoxyethylated linear fatty alcohols (e.g. Brij), polyoxyethylated castor oil (e g Cremophor), polyoxyethylated stearic acid (e g Myrj), etc.

other substances, like shellacs; waxes (e.g. carnauba wax, beeswax, glycowax, castor wax, etc); nylon; stearates (e.g. glycerol palmitostearate, glyceryl monostearate, glyceryl tristearate, stearyl alcohol, etc); lipids (e g glycerides, phospholipids, etc); paraffin; lignosulphonates; etc.

Also, combinations of these excipients are possible.

The excipients mentioned above can be toughened by introducing a plasticizer. The plasticizer can be but is not limited to the plasticizers mentioned below.

glycerin, polyethylene glycol, propylene glycol, triethyl citrate, diethyl phthalate, dibutyl phthalate, dibutyl sebacate, sorbitol, triacetin, etc Also, combinations of these plasticizers are possible.

The liquid used for the preparation of the suspension/solution/emulsion, can be a solvent for the excipients listed above and encompass, e g water or organic solvents with freezing points well above the freezing point of the medium used for freezing as exemplified below. Liquids, alone or a mixture of, suitable to make a suspension/solution/emulsion of the active substance, can then be, but are not limited to:

water (melting point (mp) 0° C.), tertiary butyl alcohol (mp 25.5° C.), cyclohexane (mp +6° C.), methylene chloride (mp −95.1° C.), acetone (mp −95.3° C.), methanol (mp −94° C.), ethanol (mp −117° C.), etc;

The cold medium can typically be a liquified gas, e.g. liquid nitrogen (boiling point −196° C.), liquid argon (boiling point −186° C.), liquid oxygen (boiling point −183° C.), or a cooled solvent well below the freezing point of the liquid in the suspension.

The mechanical strength of the microparticles is important for determining whether they will withstand processing with a polymer coating in a fluid bed.

Examining the microparticles with a microscope before and after the fluidization in a fluid bed will give an indication of their mechanical strength.

To achieve a relative measurement of mechanical strength the pressure where microparticles started to deform was evaluated. Microparticles within a certain size range (sieve fraction) were placed as a monolayer onto the surface of a probe with a certain area. Different loads (forces) were applied to the layer of microparticles for one minute.

Examination of the monolayer of microparticles before and after loading was made in a Scanning Electron Microscope to see at what load the microparticles started to deform. The pressure at which the microparticles started to deform was then calculated.

Pharmaceutically active substances suitable to form microparticles of this invention can be but are not limited to peptides, proteins, low molecular organic substances, pro-drugs, antigens, hormones.

Thus, a microparticle according to the present invention comprises one (or several) pharmaceutically active substances with one or several additional non-active substances, which are dispersed within the microsphere.

Uncoated particles can be retrieved as they are easily dissolved when they are immersed into a liquid due to their porous structure.

The microparticles obtained can be coated with a polymer to achieve either a time-controlled release, a site-controlled release or a pH-dependent release. Suitable polymers for coating can be, but are not limited to, the same type of polymers as listed above.

The coated microparticles can be put into capsules or incorporated into a tablet compressed by methods known by those skilled in the art.

The formulations produced based on the microparticles, coated or uncoated, can be given by different administration routes, such as, but not limited to, the oral, the parenteral, the nasal, the pulmonary, the rectal, the tonsillar, the buccal, the intraocular, the vaginal etc, administration routes. The preferred administrations are by the oral, nasal, pulmonary and rectal routes.

WORKING EXAMPLES

The following examples illustrate different aspects of the invention.

The size distribution of the obtained microparticles was measured by sieving. By mercury porosimetry measurements the bulk-density and pore-size distributions were determined. To determine the median pore size the pressure range for mercury intrusion corresponded to pore sizes between 0.0005 $\mu$m and 10 $\mu$m.

By subjecting a monolayer of the microparticles to compaction forces their relative strength was measured.

Example 1

Preparation of Microparticles with a High Loading of Dry Content that Withstand Coating in a Fluidized Bed A suspension containing talc powder was made according to the composition below;

| | |
|---|---|
| Talc powder (1–2 $\mu$m) | 90 g |
| Talc powder (5–80 $\mu$m) | 210 g |
| HPMC, 6 cps | 80 g |
| Tween 80 (polysorbate 80) | 6 g |
| Purified water | 750 g |

Weight percent of dry content in suspension: 34 (19.2 vol %)

First, polysorbate 80 was mixed with the water. The HPMC was then added and dissolved during stirring with subsequent addition of the substance. The suspension was then deagglomerated by high-shear mixing. The deagglomerated suspension was fed through a pneumatic nozzle with a diameter of 1.0 mm at a speed of about 15 ml/min. The pressure of the atomizer was 1 bar. The spray formed first hit the cold gas above the liquid in a vessel filled with liquid nitrogen that was stirred to get a better wetting and instantaneous freezing of the droplets. The frozen droplets have a higher density than liquid nitrogen which make them sink to the bottom of the vessel. The frozen droplets/microparticles were then placed in a conventional freeze-drier with a shelf-temperature of −20° C. The primary drying was performed stepwise at −20° C. to 0° C. at 0.1 mbar. The dry microparticles were free-flowing and spherical. Scanning Electron Microscopy showed a homogeneous distribution of the talc powder with pores (0.1–2 $\mu$m) in between. The bulk density, median pore size and mechanical strength was measured and the results are shown in table 2.

Compaction measurements showed that the microparticles obtained had a low friability (high mechanical strength).

Fluidization of the microparticles in Example 1 in a fluidized bed showed by microscopy that the microparticles did not break down. These microparticles started to deform at a pressure of 94 kPa (sieve fraction: 450–630 $\mu$m). Final coating with a polymer in a fluidized bed proved that the microparticles could be successfully coated.

Example 2

Coating of Microparticles with a Polymeric Film

The microparticles from Example 1 were easily handled without falling apart and tough enough to be successfully coated. A fraction of 20 g of the microspheres, 150–300 $\mu$m in size, were successfully coated with an enteric polymer to a film thickness of 30 $\mu$m, in a fluidized bed.

Characterization of Pellets Obtained in Example 1.

TABLE 1

Size distribution. Sieving (weight fraction %)

| Fraction | Example 1 |
|---|---|
| <100 $\mu$m | 1 |
| 100–150 $\mu$m | 2 |
| 150–300 $\mu$m | 22 |
| 300–450 $\mu$m | 32 |
| 450–630 $\mu$m | 26 |
| 630–800 $\mu$m | 12 |
| 800–1000 $\mu$m | 4 |

TABLE 2

Characterization of microparticles

| | | | Mercury porosity measurements | | |
|---|---|---|---|---|---|
| | | | | Mechanical strength | |
| Example no. | Dry content (vol %) | Binder (wt %) based on dry content | Bulk density (g/cm³) | Pore median size (μm) (measured range: 0.0005–10 μm) | Kpa | Fraction |
| 1 | 19.2 | 21 | 0.47 | 0.8 | 94 | 450–630 μm |

What is claimed is:

1. A method of preparing homogeneous microparticles comprising a pharmaceutically active substance, wherein the method uses a spray freezing technique and comprises the steps of:
   a) atomizing into droplets a liquid medium having a minimum dry content of 15% by volume and comprising:
      i) a pharmaceutically active substance;
      ii) a polymer selected from the group consisting of water soluble polymers and non-water soluble polymers, said polymer being present in an amount of at least 5 per cent by weight based upon the dry content of the medium;
      iii) a liquid in which the pharmaceutically active substance and polymer are suspended, dissolved or emulsified; and
      iv) optionally a dispersing agent;
   b) freezing the formed droplets; and
   c) sublimating the frozen liquid of the droplets to obtain dry, homogeneous microparticles.

2. The method according to claim 1, wherein the polymer of the liquid medium constitutes at least 10 weight % of the dry content.

3. The method according to claim 1, wherein the polymer of the liquid medium constitutes at least 15 weight % of the dry content.

4. The method according to claim 1, wherein the dry content of the liquid medium is from 15 to 60 vol %.

5. The method according to claim 1, wherein the dry volume content of the liquid medium is from 15 to 60 vol % and gives dry microparticles with a relative density of 15 to 60%.

6. The method according to claim 1, wherein the dry volume content of the liquid medium is from 15 to 60 vol % and gives dry microparticles with a porosity of 40 to 85 vol %.

7. The method according to claim 1, wherein the liquid medium to be spray-frozen is a suspension.

8. The method according to claim 1, wherein the liquid medium to be spray-frozen is a solution.

9. The method according to claim 1, wherein the Liquid medium to be spray-frozen is an emulsion.

10. The method according to any one of claims 1–9, wherein the content of the pharmaceutically active substance is from 60 to 95 weight % of the weight of the dried microparticles.

11. The method according to any one of claims 1–9, wherein the dry content of the medium is from 15 to 60 vol % and the content of the pharmaceutically active substance is from 60 to 95 weight % of the dried microparticles.

12. The method according to any one of claims 1–9, wherein the polymer and dispersing agent are selected from the group consisting of cellulose derivatives, polysaccharides, natural polymers, synthetic polymers, surfactants, and mixtures thereof.

13. The method according to any one of claims 1–9, wherein the polymer and dispersing agent are selected from the group consisting of shellacs, waxes, nylon, stearates, lipids, paraffin, lignosulphonates, and mixtures thereof.

14. The method according to any one of claims 1–9, wherein the liquid in which the polymer is suspended, dissolved or emulsified is selected from the group consisting of water, tertiary butyl alcohol, cyclohexane, methylene chloride, methanol, ethanol and mixtures thereof.

15. The method according to any one of claims 1–9, wherein the formed droplets are frozen by a cold medium selected from the group consisting of liquid nitrogen, liquid argon, liquid oxygen, and solvents cooled below the freezing point if the liquid in the suspension.

16. The method according to any one of claims 1–9, wherein the sublimation is performed by freeze-drying.

17. The method according to any one of claims 1–9, wherein the size distribution of the prepared microparticles is in the range from 10 to 1000 μm.

18. Microparticles prepared according to the method of any one of claims 1–9.

19. The microparticles according to claim 18 further comprising a polymeric film coating.

20. The method according to any one of claims 1–9, further comprising the step of coating the microparticles with a polymeric film coating.

21. The method according to any one of claims 1–9, wherein the content of the pharmaceutically active substance is from 75 to 90 weight % of the weight of the dried microparticles.

22. The method according to any one of claims 1–9, wherein the liquid medium further comprises one or more plasticizers.

23. The method according to claim 22, wherein the plasticizer is selected from the group consisting of glycerin, polyethylene glycol, propylene glycol, triethyl citrate, diethyl phthalate, dibutyl phthalate, dibutyl sebacate, sorbitol, tiacetin, and mixtures thereof.

* * * * *